United States Patent [19]

Thiercelin et al.

[11] Patent Number: 4,821,577
[45] Date of Patent: Apr. 18, 1989

[54] MODIFIED RING TEST

[75] Inventors: Marc Thiercelin, Cambridge, England; Jean C. Roegiers, Tulsa, Okla.

[73] Assignee: Dowell Schlumberger Incorporated, Tulsa, Okla.

[21] Appl. No.: 65,317

[22] Filed: Jun. 22, 1987

[51] Int. Cl.⁴ ............................................. G01N 19/08
[52] U.S. Cl. ........................................ 73/799; 73/153; 73/818
[58] Field of Search ................. 73/818, 825, 822, 799, 73/153, 87; 364/508

[56] References Cited

U.S. PATENT DOCUMENTS

| | | | |
|---|---|---|---|
| 3,693,419 | 9/1972 | De Pierre et al. | 73/822 X |
| 4,075,886 | 2/1978 | Barker | 73/799 X |
| 4,116,049 | 9/1978 | Barker | 73/87 |
| 4,152,941 | 5/1979 | Abou-Sayed et al. | 73/799 |
| 4,562,736 | 1/1986 | Iwasaki et al. | 73/587 |

FOREIGN PATENT DOCUMENTS

| | | | |
|---|---|---|---|
| 1161964 | 9/1958 | France | 73/818 |
| 0879369 | 11/1981 | U.S.S.R. | 73/818 |
| 1200159 | 12/1985 | U.S.S.R. | 73/818 |

*Primary Examiner*—Eugene R. LaRoche
*Assistant Examiner*—Seung Ham
*Attorney, Agent, or Firm*—Stephen A. Littlefield

[57] ABSTRACT

A novel test specimen configuration and modified ring test method for determining the fracture toughness, $K_{Ic}$, using rock core is disclosed. The use of a truncated hollow cylindrical specimen under compressive load avoids the development of a large process zone (micro-cracked region) during testing, thus allowing accurate fracture toughness measurements on subsized specimens. Results using soft sandstones and Indiana limestone validate the procedure.

2 Claims, 3 Drawing Sheets

MODIFIED RING TEST

BACKGROUND OF THE INVENTION

1. Field of the Invention

This invention relates to a method and specimen configuration for measuring the true (as opposed to "apparent") fracture toughness on small sized core specimens. More specifically, the invention relates to a modified ring test that accurately measures rock toughness using small size specimens.

2. Description of the Prior Art

It is generally accepted that rock fracturing is of fundamental importance in several oil and gas well completion services: drilling, hydraulic fracturing (i.e., the pumping of fluids into a well in order to fracture the reservoir and increase hydrocarbon production) and borehole stabilizing (i.e., preventing the collapse of the well bore during completion, stimulation and production). As such, an accurate and reliable quantitative measurement of rock fracture toughness is necessary to perform rock fracture simulation studies utilizing contemporary mathematical modeling such as pseudo-three dimensional simulators and the like.

The stress intensity factor approach is commonly used in three-dimensional hydraulic fracturing models. The stress intensity factor is a measurement of the stress singularity near the crack tip. The pertinent criterion for propagation is that fracture will propagate once the stress intensity factor, $K_I$, is equal to or greater than a critical value, $K_{Ic}$. $K_{Ic}$ is referred to as the fracture toughness and is a material property. Generally, the stress intensity factor is viewed as a function of the geometry of the crack, the geometry of the body, and the loading parameters (i.e., fluid pressure in the fracture and confining pressure) while the toughness is viewed as a function of the rock type only. For a more detailed explanation of the stress intensity factor, see G. R. Irwin, "Analysis of Stresses and Strains Near the End of a Crack Traversing a Plate", Journal of Applied Mechanics, 24 (1957): 361-4 and G. R. Irwin & R. de-Wit, "A Summary of Fracture Mechanics Concepts", Journal of Testing and Evaluation, 11 (1983): 56-65 herein incorporated by reference for such purpose.

The stress intensity approach assumes that the rock behaves as a linear elastic material. This assumption is acceptable if the zone of non-linear behavior, ahead of the fracture tip, is small in comparison to the other geometric dimensions, including the crack length. The non-linear zone is due to microcrack formation as a consequence of extreme stress concentrations in the immediate vicinity of the crack tip. Experimental results on rocks have shown that linear elasticity is an acceptable assumption if the crack length is greater than 100 to 200 millimeters. These dimensional limitations imply that field scale fractures (of great length) can be evaluated using linear elastic theory; whereas, in laboratory testing, the determination of $K_{Ic}$ is carried out on more modest length specimens; hence care must be taken to avoid or account for non-linearity. In other words, in order to obtain a valid measurement of toughness in the laboratory, the size of the process zone (i.e., the non-linear zone) should be small compared to the initial notch length. Such a requirement is often difficult to meet, particularly when a typical rock core is used as the specimen and consequently, accurate toughness determinations may not be achieved. For example, when using the prior art three point bending tests and-/or center notched panel tests (see FIG. 4), a relatively large process zone ahead of the crack tip makes the apparent toughness size dependent. Consequently, underestimation of the actual toughness, $K_{Ic}$, when using the prior art methods on subsidized specimens, will frequently occur.

Thus, prior to the present invention, a need for a test procedure that measures the fracture toughness in a manner that is virtually independent of the test configuration and, in particular, the size of the specimen, existed. Ideally, such a test procedure would further allow for determination of $K_{Ic}$ at representative in-situ stresses and environmental conditions. The modified ring test method and novel specimen configuration, according to the present invention, is felt to satisfy these needs.

SUMMARY OF THE INVENTION

The present invention represents a modified ring test method of measuring rock fracture toughness. Fracture toughness is an important factor in rock fracture simulation in that the fracture geometry depends rather sharply on toughness. Thus, contemporary mathematical modeling or other mathematical predictive and interpretive analyses will be dependent upon access to accurate and reliable toughness data. In light of the previously mentioned problems associated with the specimen "size-dependency" of prior art methods of measuring fracture toughness, the present invention is viewed as providing an improved specimen configuration and method capable of direct measurement of fracture toughness using a conventionally sized rock core.

Thus, the present invention provides a method of determining the fracture toughness, $K_{Ic}$, comprising the steps of:

(a) preparing a cylindrical specimen, wherein the cylindrical specimen is characterized by the presence of a circular opening therethrough and two diametrically opposed flat surfaces of the same length on the external radius of the cylindrical specimen;

(b) applying a compressive displacement at a constant rate on the two diametrically opposed flat surfaces;

(c) monitoring the load applied to the specimen resulting from the compressive displacement of step (b) as a function of displacement;

(d) measuring the value of the critical load, $F_c$, corresponding to the minimum value of the load applied as a function of displacement in step (c) at critical crack length; and (e) multiplying the value of the stress intensity factor per unit load for this critical crack length, $K_f$, times the value of the critical load, $F_c$, from step (d) to establish the fracture toughness, $K_{Ic}$, according to the formula:

$$K_{Ic} = K_f \times F_c.$$

The novel test specimen, according to the present invention, comprises a cylindrical shape with a circular hole passing therethrough and with two diametrically opposed flat surfaces of the same length located on the external radius of the cylindrical shape. Preferably, the cylindrical test specimen employed in the present invention is a conventional rock core.

It is the object of the present invention to provide a novel specimen configuration to be used in a novel modified ring test method for measuring rock fracture toughness. It is a further object to provide such a novel test specimen and modified ring test toughness measurement method that is virtually specimen "size-independent", particularly when employing a conventional cylinder rock core as the source of the specimen. It is still a further object of the present invention to provide a modified ring test method of measuring fracture toughness wherein the toughness data measured using a conventional rock core as the specimen is reliable for use in contemporary rock fracture simulation programs and predictive calculations or the like. Further objects of the present invention will be apparent upon complete reading of the specifications taken in conjunction with the attached drawings and claims.

DESCRIPTION OF THE PREFERRED EMBODIMENTS

Figure 1:
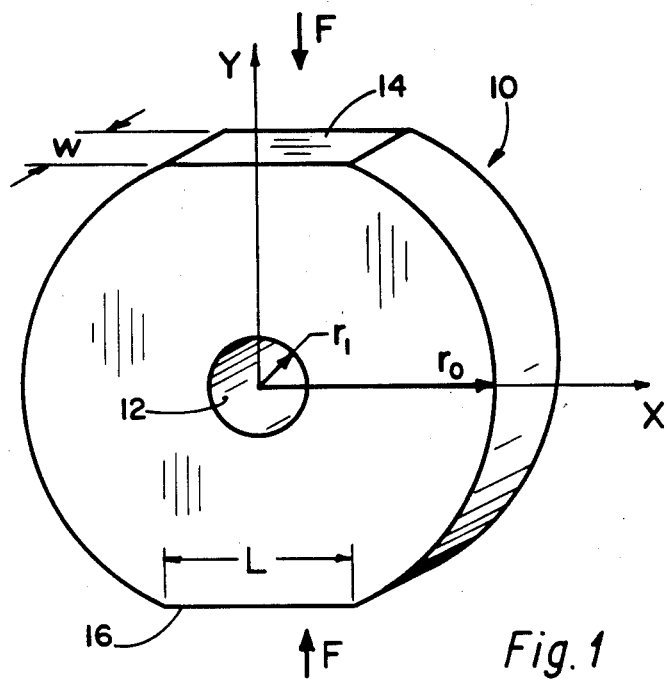
FIG. 1 is a perspective side view of the novel specimen configuration, according to the present invention.

The improved test specimen configuration and modified ring test procedure, according to the present invention, how they differ from the prior art, and the advantages associated with their use can perhaps be best explained and understood by reference to the drawings. FIG. 1 illustrates a typical specimen configuration according to the present invention. As illustrated, the test specimen, generally designated by the number 10, to be used in the modified ring test procedure, is a truncated cylindrical disk with a circular opening 12 centrally located about the axis of rotation of the cylinder. Thus, the configuration of the specimen can essentially be characterized by defining or specifying a major radius $r_o$ (the radius of the outer cylinder), a minor radius $r_1$ (the radius of the opening) and a width w (height of the cylinder). As further illustrated, the physical configuration of the specimen, according to the present invention, is further characterized by the presence of two diametrically opposed (i.e., parallel, but opposite sides) flat surfaces 14 and 16 of same length, L, on the external radius of the cylindrical specimen 10. During testing and as vectorially suggested in FIG. 1, the two diametrically opposed flat surfaces 14 and 16 are subjected to compressive loading, F, thus defining the relative loading axis y and the associated orthogonal direction or axis x.

Traditionally, it has been assumed that the initial notch length requirement of prior art methods for measuring fracture toughness is specimen shape independent. However, according to the present invention, if one considers that the size of the process zone is greater than the size of the stress singularity (i.e., at the laboratory scale), the laboratory testing will lead to an "apparent toughness" value, which will strongly depend on how much energy has been wasted creating this non-linear cracked cloud. Moreover, the size of this process zone is dependent on the specimen geometry. Thus, the present invention can be viewed as providing an optimum specimen geometry that allows small size specimens to be used for accurate $K_{Ic}$ determination, since the extension of the process zone is so limited that it becomes negligible. Thus, in a broad sense, the scope of the present invention involves any measurement of fracture toughness on any material (i.e., by way of example, but not limited thereto, rock, concrete, glass, ceramic and/or the like) wherein the relative size of the process zone influences the results of the measurement. In particular, the test procedure can be advantageously performed on conventional rock core specimens with minimal sample preparation.

The basic principle of the test method, according to the present invention, is to create a confining state of stress ahead of the crack tip in order to prevent the development of the process zone. This confinement is induced by the geometry of the loading surface where slippage is prevented. The inner hole acts as a stress concentrator; hence the crack initiates at the inner hole wall and propagates along the loading axis. Preferably, the test specimen of FIG. 1 is to be placed in a conventional compression machine, as generally known in the art, or the equivalent. Conveniently, the specimen is held in a rigid or stiff load frame (optionally confined in a controlled environment). A compressive force is then applied perpendicular to the load surfaces 14 and 16 such as to preferably produce a constant displacement rate, ds/dt. The load applied to the test specimen is then monitored and preferably recorded and displayed in a manner as illustrated in FIG. 2.

Figure 2:
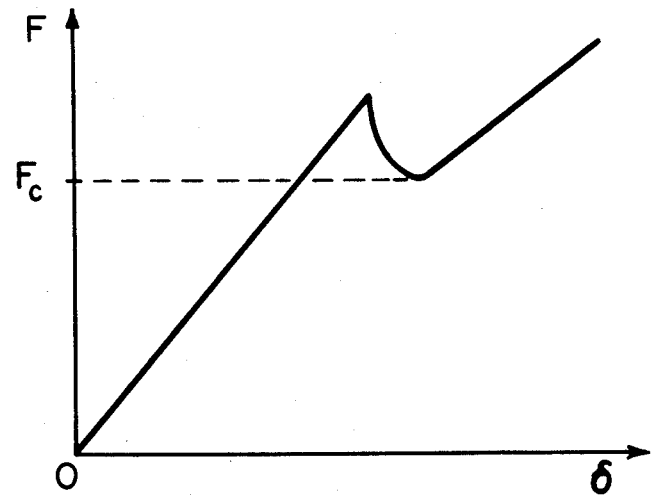
FIG. 2 is a typical load versus displacement plot, according to the present invention, illustrating a discontinuity and associated relative minimum in the load value which is then used to compute the fracture toughness.

As shown in FIG. 2, a typical load versus displacement curve will exhibit a minimum during the fracture propagation. This minimum in the load value corresponds to a "critical" effective crack length where the fracture switches from an unstable to a stable propagation state. For purposes associated with this invention, the crack length associated with this process is referred to as the critical crack length. This behavior is the consequence of the sample geometry and boundary conditions. For purposes of this invention, the minimum of the load value, $F_c$, is referred to as critical load and is directly proportional to the desired fracture toughness, $K_{Ic}$, according to the formula: $K_{Ic} = K_f \times F_c$, wherein the proportionality constant $K_f$ is referred to for purposes of this invention as the stress intensity factor per unit load for the critical crack length, and $F_c$ is normalized by dividing the force by the specimen thickness, w (see FIG. 1), and is expressed in force/length units.

Figure 3:
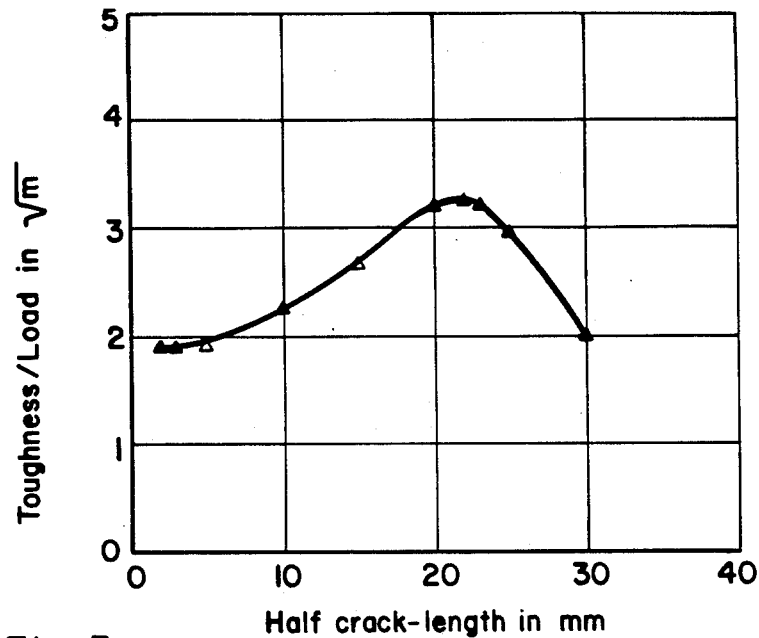
FIG. 3 is a plot of toughness per unit load versus half crack length for a specimen according to FIG. 1.

In principle, the value of the so-called stress intensity factor per unit load for this "critical" crack length, $K_f$, is a function of the geometrical parameters and Poisson's ratio of the specimen. In practice, the value of the stress intensity factor per unit load, $K_f$, has to be computed or established empirically or semi-empirically, prior to the computation of the $K_{Ic}$, using the above mathematical equation. Preferably, this stress intensity factor per unit load as a function of the crack length is to be computed using the displacement discontinuity method as described by S. L. Crouch and A. N. Starfield, "Boundary Element Methods in Solid Mechanics", Allen and Unwin Publishers (1983), herein incorporated by reference. To further illustrate this concept, a numerical result showing a critical crack length of 22 mm for a specimen with an internal diameter of 10 mm, an external diameter of 77 mm, an 18 mm loading surface and Poisson's ratio of 0.25 is plotted in FIG. 3. The significance of this curve is the existence of a crack length for which the stress intensity factor is maximum. During the fracture toughness measurement, this critical crack length will be obtained when the load is at its minimum value. Thus, the toughness measurements, according to the present invention, are performed at this critical crack length.

Figure 5:
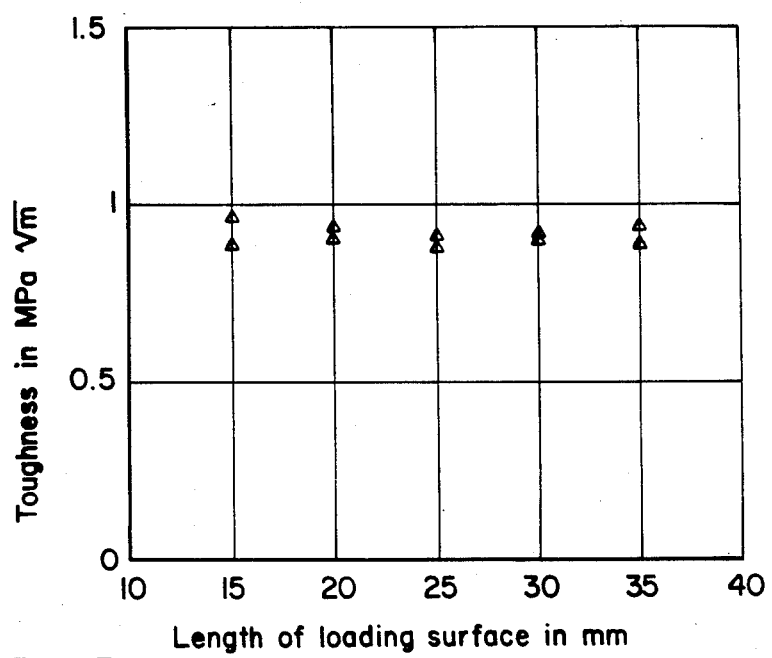
FIG. 5 illustrates a plot of toughness measurement, according to the present invention, as a function of length of the loading surface.
Figure 4:
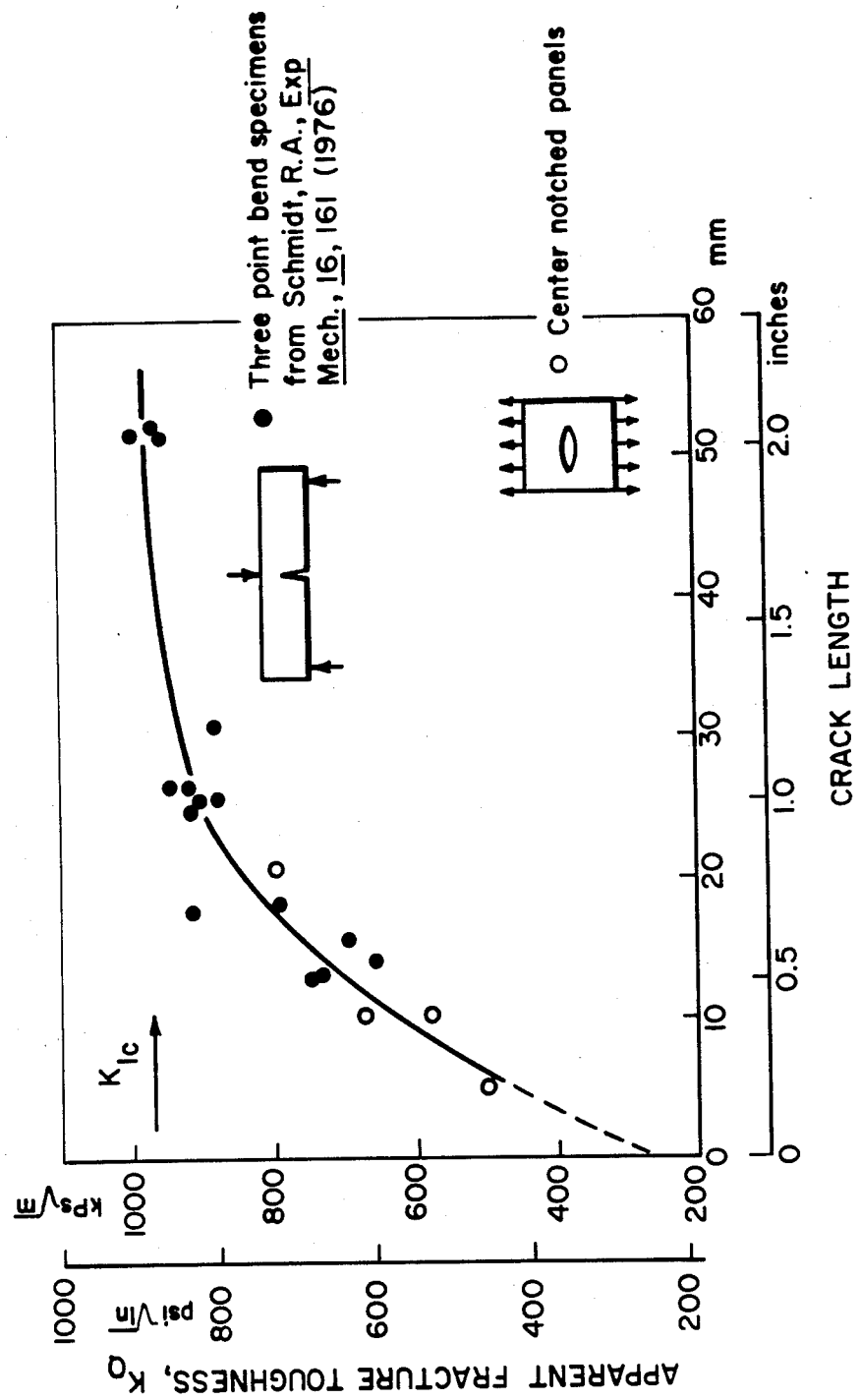
FIG. 4 is a typical plot of toughness as a function of length, according to prior art methods of measuring toughness.

To further verify the reliability of the toughness measurement according to the present invention, toughness measurements as a function of the length of the loading surface, L, and at the critical length have been performed on a soft sandstone. The results are shown in FIG. 5 and confirm that the toughness measurement is crack length independent. Toughness measurements have also been performed on Indiana limestone. Data obtained with sufficiently large samples reported in the literature indicate a toughness of $0.99 + 0.05$ $MP_a$ m. The modified ring test procedure according to the present invention indicated a toughness of $1.05 + 0.04$ $MP_a$ m. Consequently, it is concluded that the modified ring test procedure and novel specimen geometry according to the present invention, is not subsized and allows one to determine toughness on a conventional core based specimen geometry.

The advantages associated with the present invention are considered significant, particularly relative to the problems associated with the prior art methods of measuring fracture toughness on standard size oil and gas well rock core. The measurement technique is viewed as being unique in that it is virtually specimen "size-independent". As such, the method produces reliable data that can be readily extrapolated to field situations. More specifically, the method of measuring fracture toughness, according to the present invention, exhibits the advantage of requiring only standard size cores. It is this particular unexpected feature that serves to readily distinguish the method of measuring fracture toughness of the present invention from the prior art methodologies. The present invention further exhibits the advantage of being capable of being performed under simulated downhole conditions.

Having thus described the invention with a certain degree of particularity, it is to be understood that the invention is not limited to the embodiments set forth herein for purposes of exemplification, but is to be limited only by the scope of the attached claims, including a full range of equivalents to which each element thereof is entitled.

We claim:

1. A method of determining the fracture toughness, $K_{Ic}$, comprising the steps of:
    (a) preparing a cylindrical specimen having a longitudinal axis and a cylindrical outer surface, wherein said cylindrical specimen is characterized by the presence of a cylindrical opening therethrough having a common axis with said longitudinal axis, and two diametrically opposed flat surfaces of the same length on said cylindrical outer surface of said cylindrical specimen;
    (b) applying a compressive displacement at a constant rate on said two diametrically opposed flat surfaces;
    (c) monitoring the load applied to said specimen resulting from said compressive displacement of step (b) as a function of displacement;
    (d) measuring the value of the critical load, $F_c$, corresponding to the minimum value of the load applied as a function of the displacement in step (c), at critical crack length; and
    (e) Multiplying the value of the stress intensity factor per unit load for this critical crack length, $K_f$, times the value of the critical load, $F_c$, from step (d) to establish the fracture toughness, $K_{Ic}$, according to the formula:

$$K_{Ic} = K_f \times F_c.$$

2. A method of determining the fracture toughness according to claim 1 wherein said cylindrical specimen is a rock core.

* * * * *